US006582914B1

(12) United States Patent
Caldwell et al.

(10) Patent No.: US 6,582,914 B1
(45) Date of Patent: Jun. 24, 2003

(54) METHOD FOR GENERATING A LIBRARY OF OLIGONUCLEOTIDES COMPRISING A CONTROLLED DISTRIBUTION OF MUTATIONS

(75) Inventors: Robert M. Caldwell, Belmont, CA (US); Volker Schellenberger, Palo Alto, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/699,250

(22) Filed: Oct. 26, 2000

(51) Int. Cl.[7] ............................. C12Q 1/68; C12P 19/34
(52) U.S. Cl. .................. 435/6; 435/91.1; 435/91.2
(58) Field of Search ................... 435/6, 91.1, 91.2

(56) References Cited

U.S. PATENT DOCUMENTS

| | | | |
|---|---|---|---|
| 5,093,257 A | 3/1992 | Gray | 435/202 |
| 5,270,170 A | 12/1993 | Schatz et al. | 435/7.39 |
| 5,521,077 A | 5/1996 | Khosia et al. | 435/172.3 |
| 5,556,747 A * | 9/1996 | Kumar | 435/6 |
| 5,830,696 A | 11/1998 | Short | 435/69.1 |
| 6,251,604 B1 * | 6/2001 | Lietz | 435/6 |

FOREIGN PATENT DOCUMENTS

| | | |
|---|---|---|
| EP | 0 563 103 B1 | 12/1991 |
| EP | 0 466 083 A2 | 1/1992 |
| WO | WO 87/01374 | 3/1987 |
| WO | WO92/02536 * | 2/1992 |
| WO | WO 97/07205 | 2/1997 |
| WO | WO 97/15657 | 5/1997 |
| WO | WO 97/46670 | 12/1997 |
| WO | WO 98/05765 | 2/1998 |
| WO | WO 98/10102 | 3/1998 |
| WO | WO 98/17684 | 4/1998 |
| WO | WO 98/28416 | 7/1998 |
| WO | WO 98/41622 | 9/1998 |
| WO | WO 98/41623 | 9/1998 |
| WO | WO 98/41653 | 9/1998 |
| WO | WO 09/42832 | 10/1998 |
| WO | WO 98/51802 | 11/1998 |

OTHER PUBLICATIONS

Perlak, F. J., "Single step large scale site–directed in vitro mutagenesis using multiple oligonucleotides", Nucl. Acids Res., vol. 18, pp. 7457–8 (1990).*

Hermes J. D. et al., "Searching sequence space by definably random mutagenesis: Imroving the catalytic potency of an enzyme", PNAS USA, vol. 87, pp. 696–700 (1990).*

Aslanidis et al., Ligation–independent cloning of PCR products (LIC–PCR), *Nucleic Acids Research*, V. 18, No. 20 pp. 6069–6074 (1990).

Bashkirov, V., et al., "Interplasmidic illegitimate recombination in *Bacillus subtilis*," *Mol Gen Genet*, V.1, 213 pp. 465–470 (1988).

Beck et al., "Introduction of arbitrary sequences into genes by use of class IIs restriction enzymes," *Nucleic Acids Research*, V. 22, N. 5, pp. 886–887 (1994).

(List continued on next page.)

*Primary Examiner*—Kenneth R. Horlick
*Assistant Examiner*—Teresa Strzelecka
(74) *Attorney, Agent, or Firm*—Genencor International, Inc

(57) ABSTRACT

Methods are disclosed for producing libraries of nucleic acid molecules which libraries are derived from a nucleic acid template. The libraries comprise variant nucleic acids which are produced from a mutagenesis strategy using, e.g., a plurality of defined mutagenic and/or non-mutagenic primers and specific reaction conditions which favor the production of varied combinatorial mutants.

10 Claims, 2 Drawing Sheets

OTHER PUBLICATIONS

Berger, S. et al, "Phoenix Mutagenesis: One–Step Reassembly of Multiply Cleaved Plasmids with Mixtures of Mutant and Wild–Type Fragments," *Analytical Biochemistry,* 214, pp. 571–579 (1993).

Bron, S. et al, "Ultraviolet Inactivation and Excision–Repair in *Bacillus Subtilis,*"*Mutation Research,* 15 pp. 1–10 (1972).

Canosi. U. et al, "Plasmid Transformation in *Bacillus Subtilis*: Effects of Insertion of *Bacillus Subtilis* DNA into Plasmid pC 194," *Mol Gen Genet,* 181, pp. 434–440 (1981).

Cheng, S. et al, "Effective amplification of long targets from cloned inserts and human geonomic DNA," *Proc. Natl. Acad. Sci. USA,* V.91, pp. 5695–5699 (1994).

Contente, S. et al, "Marker Rescue Transformation by Linear Plasmid DNA in *Bacillus Subtilis,*" *Plasmid,* 2, pp. 555–571 (1979).

Crameri, A. et al, "DNA shuffling of a family of genes from diverse species accelerates directed evolution," *Nature,* V.391, pp. 228–291 (1998).

Crameri et al., "Combinatorial Multiple Cassette Mutagenesis Creates All the Permutations of Mutant and Wild–Type Sequences," *Benchmarks,* V. 18, No. 2, pp. 194–196 (1995).

Dustin, M. et al, "A novel Mutagenesis Strategy Identifies Distantly Spaced Amino Acid Sequences the are Required for the Phosphorylation of Both the Oligosaccharides of Procathepsin D by N–Acetylglucosamine 1–Phosphotransferase," *The Journal of Biological Chemistry,* V.270, No.1, pp. 170–179 (1995).

Guerout–Fleury, A. et al, "Plasmids for ectopic integration in *Bacillus subtilis,* " *Gene,* 180, pp. 57–61 (1996).

Hall, Berry G., "Changes in the substrate specificities of an Enzyme during Directed Evolution of New Functions," *Biochemistry,* 20, pp. 4042–4049 (1981).

Horton, R. M. et al, "Engineering hybrid genes without the use of restriction enzymes: gene splicing by overlap extension," *Gene,* 77, pp. 61–68 (1989).

Iglesias, A. et al, "Plasmid Transformation in *Bacillus subtilis:* Symmetry of gene conversion in Transformation with a Hybrid Plasmid Containing Chromosomal DNA," *Mol Gen Genet,* 189, pp. 73–76 (1983).

Jansen, R. et al, "Disruption of phase during PCR amplification and cloning of heterozygous target sequences," *Nucleic Acids Research,* V.18, No. 17 pp. 5153–5156 (1990).

Judo, M. et al, "Stimulation and suppression of PCR–mediated recombination," *Nucleic Acids Research,* vol.26, No. 7, pp. 1819–1825 (1998).

Kuijper et al., "Functional cloning vectors for use in directional cDNA cloning using cohesive ends produced with T4 DNA polymerase," *GENE,* issue 06325, PP. 147–155 (1992).

Lebedenko, et al., "Method of artificial DNA splicing by directed ligation (SDL)," *Nucleic Acids Research,* V. 19, N. 24, pp. 6757–6751 (1991).

Ling et al., "Approaches to DNA Mutagenesis An Overview," *Analytical Biochemistry,* V. 254, 157–178 (1997) Article No. AB972428.

Kuchner, O. et al, "Directed evolution of enzyme catalysts," *TIB Tech,* vol. 15, 9 pages (1997).

Markland et al., "Iterative Optimization of High–Affinity Protease Inhibitors Using Phage Display. 1 Plasmin," *Biochemistry,* V. 35, pp. 8045–8057 (1996).

Marton, A. et al, "DNA nicking favors PCR recombination," *Nucleic Acids Research,* vol. 19, No. 9, pp. 2423–2426 (1991).

Merino et al., "A General, PCR–Based Method for Single or Combinatorial Oligonucleotide–Directed Mutagenesis on pUC/M13 Vectors," *BioFeedback,* V. 12, No. 4, pp. 508–510 (1992).

Meyerhans, A. et al, "DNA recombination during PCR," *Nucleic Acids Research,* vol. 18, No. 7, pp. 1687–1691 (1990).

Michel, B. et al., "Intramolecular recombination during plasmid transformation of *Bacillus subtilis* competent cells," *The EMBO Journal,* vol. 1, No. 12, pp. 1565–1571 (1982).

Michel, B. et al, "Intermolecular recombination during Transformation of *Bacillus subtilis* Competent Cells by Monomeric and Dimeric Plasmids," *Plasmid,* 10, pp. 1–10 (1983).

Ness, J. et al, "DNA shuffling of subgenomic of subtilisin," *Nature Technology,* vol. 17, pp. 893–896 (1999).

Niaudet, B. et al., "Insertional mutagenesis in *Bacillus subtilis:* mechanism and use in gene cloning," *Gene,* 19, pp. 277–284 (1982).

Noirot, M.–A. et al, "Plasmid Replication Stimulates DNA Recombination in *Bacilius subtilis,* " *J. Mol. Biol.,* 196, pp. 39–48 (1987).

Odelberg, S. et al, "Template–switching during DNA synthesis by Thermus aquaticus DNA polymerase 1," *Nucleic Acids Research* vol.23, No. 11, pp. 2049–2057 (1995).

Osuna et al., "Combinatorial mutagenesis of three major groove–contacting residues of EcoRI: single and double amino acid replacements retaining methyltransferase–sensitive activities," *GENE,* v. 106 pp. 7–12 (1991).

Paabo, S. et al, "DNA Damage Promotes Jumping between Templates during Enzymatic Amplification," *The Journal of Biological Chemistry,* vol.265, No.8, pp. 4718–4727 (1990).

Padgett et al., "Creating seamless junctions independent of restriction sites in PCR cloning," *GENE,* v. 168 pp. 31–35, (1996).

Peck, Joel R., "A Ruby in the Rubbish: Beneficial Mutations, Deleterious Mutations and the Evolution of Sex," *Genetics,* 137, pp. 597–606 (1994).

QuikChange ™ Site–Directed Mutagenesis Kit, *Stratagene.*

Rudolph, C. et al, "Transformation of *Bacillus subtilis* by Single–Stranded Plasmid DNA," *Journal of Bacteriology,* vol. 165, No. 3, pp. 1015–1018 (1986).

Schluga, A. et al, "An approach to construction of Hybrid Polypeptide molecules–homologue recombination method," *Nucleic Acids Research,* vol. 22, No. 18, pp. 3808–3810 (1994).

Shao, Z. et al, "Random–priming in vitro recombination: an effective tool for directed evolution," *Nucleic Acids Research,* vol.26, No. 2, pp. 681–683 (1998).

Shi, X.–B. et al, "Rapid PCR Construction of a Gene Containing Lym–1 Antibody Variable Regions," *PCR Methods and Applications,* pp. 46–53 (1993).

Stemmer, William P.C., "DNA shuffling by random fragmentation and reassembly: in vitro recombination for molecular evolution," *Proc. Natl. Acad. Sci. USA,* vol.91, pp. pp. 10747–10751 (1994).

Stemmer, William P.C., "Searching Sequence Space: Using recombination to search more effectively and thoroughly instead of making bigger combinatorial libraries," *Bio/Technology,* vol. 13, pp. 549–553 (1995).

Stoker, "Cloning of PCR products after defined cohesive termini are created with T4 DNA Polymerase," *Nucleic Acids Research,* V. 18, No. 14, pp. 4290, (1990).

Szybalski et al., "Class–IIS restriction enzymes—a review," *GENE,* v. 100, PP. 13–26 (1991).

Tawfik, D. et al, "Man–made cell–like compartments for molecular evolution," *Nature Biotechnology,* vol. 16, pp. 652–656 (1998).

Tseng, DNA Cloning without Restriction Enzyme and Ligase, *Research Report,* V. 27, No. 6 pp. 1240–1244, (1999).

Tu et al., "Generation of a Combination of Mutations by Use of Multiple Mutagenic Oligonucleotides," *Benchmarks,* V. 20, N. 3, pp. 352–353.

Wu et al., Humanization of a Murine Monoclonal Antibody by Simultaneous Optimization of Framework and CDR Resides, *J. Mol. Biol.,* V. 294, pp. 151–162, (1999).

Young, Michael, "The Mechanism of Insertion of a Segment of Heterologous DNA into the Chromosome of *Bacillus subtilis,*" *Journal of General Microbiology,* 129, pp. 1497–1512 (1983).

Zhang, J.–H. et al, "Directed evolution of a fucosidase from a galatosidase by DNA shuffling and screening," *Proc. Natl. Acad. Sci. USA,* vol.94, pp. 4504–4509 (1997).

Zhao, H. et al., "Optimization of DNA shuffling for high fidelity recombination," *Nucleic Acids Research,* vol.25, No. 6, pp. 1307–1308 (1997).

Zhao, H. et al, "Molecular evolution by Staggered extension process (StEP) in vitro recombination," *Nature Biotechnology,* vol. 16, pp. 258–261 (1998).

Zoller, "New Recombinant DNA methodology for protein engineering," *Current Biology Ltd.,* 3:348–354 (1992).

Ge, Liming et al., "Simultaneous Introduction of Multiple Mutations Using Overlap Extension PCR," *Biotechniques,* Eaton Publishing, Natick, U.S., vol. 22, No. 1, 1997, pp. 29–30.

Horton, Robert M. et al., "Engineering hybrid genes without the use of restriction enzymes: gene splicing by overlap extension," *Gene,* Elsevier Biomedial Press, Amsterdam, NL, vol. 77, 1989, pp. 61–68, XP002090392.

Ito, Wataru et al., "A general method for introducing a series of mutations into cloned DNA using the polymerase chain reaction," *Gene,* Elsevier Biomedical Press, Amsterdam, NL, vol. 102, No. 1, 1991, pp. 67–70, XP000303855.

Lee, Nancy et al., "Site–Specific Mutagenesis Method Which Completely Excludes Wild–Type DNA from the Transformants," *Applied and Environmental Microbiology,* vol. 57, No. 10, 1991, pp. 2888–2890, XP002216326.

Perlak, Frederick, "Single step large scale site–directed *in vitro* mutagenesis using multiple oligonucleotides," *Nucleic Acids Research,* Oxford University Press, Surrey, GB, vol. 18, No. 24, 1990, pp. 7457–7458, XP002090393.

Sandhu, Gurpreet, et al., "Dual Asymmetric PCR One–Step Construction of Synthetic Genes," *Biotechniques,* vol. 12, No. 1, 1992, pp. 14–15, XP002216325.

Sutherland, Lesley et al., "Multisite Oligonucleotide–Mediated Mutagenesis: Application to the Conversion of a Mitochondrial Gene to Universal Genetic Code," *Biotechniques,* Eaton Publishing, Natick, U.S., vol. 18, No. 3, 1995, pp. 458, 460, 463–464, XP002147661.

Xiao., Gutian et al., "Construction and Screening of a Multi–Point Site–Specific Mutant Library of Subtilisin E with a Set of Oligonucleotides,", *Science in China,* Series C, Life Science, Gordon and Breach, Amsterdam, NL, vol. 40, No. 4, Aug., 1997, pp. 337–344, XP002090393.

Weisberg, Edward P. et al., "Simultaneous Mutagenesis of Multiple Sites: Application of the Ligase Chain Reaction Using PCR Products Instead of Oligonucleotides," *Biotechniques,* Eaton Publishing, Natick, U.S., vol. 15, No. 1, Jul., 1993, pp. 68–70, 72–74, XP000385832.

\* cited by examiner

METHOD FOR GENERATING A LIBRARY OF OLIGONUCLEOTIDES COMPRISING A CONTROLLED DISTRIBUTION OF MUTATIONS

BACKGROUND OF THE INVENTION

A. Field of the Invention

The present invention is related to the generation of libraries of mutant nucleic acid molecules from a precursor nucleic acid template or templates. The mutant library is then useful for selecting or screening purposes to obtain improved nucleic acid, protein or peptide product. More particularly, the present invention provides a novel method for the generation of combinatorial mutations.

B. Description of the State of the Art

Developing libraries of nucleic acids that comprise various combinations of several or many mutant or derivative sequences has recently been recognized as a powerful method of discovering novel products having improved or more desirable characteristics. A number of powerful methods for mutagenesis have been developed that when used iteratively with focused screening to enrich the useful mutants is know by the general term directed evolution.

For example, a variety of in vitro DNA recombination methods have been recently developed for the purpose of recombining more or less homologous nucleic acid sequences to obtain novel nucleic acids. For example, recombination methods have been developed comprising mixing a plurality of homologous, but different, nucleic acids, fragmenting the nucleic acids and recombining them using PCR to form chimeric molecules. For example, U.S. Pat. No. 5,605,793 generally comprises fragmentation of double stranded DNA molecules by DNase I. U.S. Pat. No. 5,965,408 generally relies on the annealing of relatively short random primers to target genes and extending them with DNA polymerase. Each of these disclosures relies on polymerase chain reaction (PCR)-like thermocycling of fragments in the presence of DNA polymerase to recombine the fragments. Other methods have taken advantage of the phenomenon known as template switching, described in, e.g., Meyerhans, A., J.-P. Vartaanian and S. Wain-Hobson (1990) *Nucleic Acids Res.* 18, 1687–1891. One shortcoming of these PCR based recombination methods however is that the recombination points tend to be limited to those areas of relatively significant homology. Accordingly, in recombining more diverse nucleic acids, the frequency of recombination is dramatically reduced and limited.

In many contexts, it is desirable to be able to develop libraries of mutant molecules that mix and match mutations which are known to be important or interesting due to functional or structural data. Several strategies toward combinatorial mutagenesis have been developed. In Stemmer et al., Biotechniques, vol. 18, no. 2 pp. 194–196 (1995), the authors use their "gene shuffling" methods in combination with a mixture of specifically designed oligonucleotide primers to incorporate desired mutations into the shuffling scheme. In another example, Osuna et al., Gene, vol. 106, pp. 7–12 (1991) designed an experiment in which synthetic DNA fragments comprising 50% wild type codon and 50% of an equimolar mixture of codons for each of the 20 amino acids at positions 144, 145 and 200 of EcoRI endonuclease. The mutagenic primers were added to a solution of ssDNA template and the primers for the 144 and 145 mutations used separately from the primers for the 200 site. The separate mixtures from each experiment were hybridized to the template ssDNA and extended for one hour with Polik polymerase. The fragments were isolated and ligated to produce a full length fragment with mutations at all three sites. The fragment was amplified with PCR and purified and cloned into a vector. While Osuna predicted that a balanced distribution of each of the 20 mutants would be obtained at each position, the authors were unable to verify whether the predicted distribution was attained. Tu et al., Biotechniques, vol. 20, no. 3, pp 352–353 (1996) describes a method for generation of combination of mutations by using multiple mutagenic oligonucleotides which are incorporated into a mutagenic polynucleotide by a single round of primer extension followed by ligation. Merino et al., Biotechniques, vol. 12, no. 4, pp. 508–509 (1992) describes a method for single or combinatorial directed mutagenesis which utilizes a universal set of primers complementary to the areas that flank the cloning region of the pUC/M13 vectors used in the mutagenesis scheme for the purpose of optimizing yield of mutants. In PCT Publication No. WO 98/42728 (California Institute of Technology) several variations on the theme of recombination of related families of nucleic acids are described. In particular, the authors describe the use of defined primers in combination with recombination based generation of diversity, the defined primers being used to encourage cross-over recombination at sites not otherwise likely to be cross-over points.

While it is apparent that a number of methods exist, it is desirable to develop further and more efficient methods of producing libraries of mutant nucleic acids and particularly for combinatorial mutagenesis. For example, significant advantages accrue from the ability to develop customized mutant nucleic acid libraries which have designed specific biases towards certain mutations. In addition, it is desirable to introduce contiguous and discontiguous mutations in a simple straightforward manner, as opposed to many current processes for discontiguous combinatorial mutation which are particularly cumbersome.

In the present invention, the inventors herein have determined a method for the combinatorial mutagenesis of nucleic acids which allows for optimization of the mutational scheme based on knowledge of the function and/or structure of the protein, while still developing a significant number of mutants with the potential for dramatically improved performance.

SUMMARY OF THE INVENTION

According to the present invention, a method of producing a library of mutant nucleic acid molecules is provided comprising the steps of: (a) obtaining a template nucleic acid; (b) preparing an oligonucleotide primer pair corresponding to the ends of said said template nucleic acid; (c) preparing two mutagenic oligonucleotide primers corresponding to a first and a second desired mutation within said template nucleic acid; (d) mixing the oligonucleotide primers prepared in said steps (b) and (c); (e) combining said mixture in said step (d) with the template nucleic acid under conditions to facilitate the polymerase chain reaction, wherein said mutagenic oligonucleotides are present in a concentration that is less than saturation concentration.

In a preferred embodiment, the template nucleic acid is a single nucleic acid. In another preferred embodiment of the invention, the mixture of oligonucleotide primers further includes non-mutagenic oligonucleotide primers corresponding to either or both of said first and second oligonucleotides. In a further preferred embodiment of the invention, the primers are added in a pre-defined ratio.

In a another embodiment of the invention, the invention comprises a method of producing a library of mutant nucleic acid molecules comprising the steps of obtaining a template nucleic acid; preparing an oligonucleotide primer corresponding to a first desired mutation within said template nucleic acid; preparing an oligonucleotide primer corresponding to a second desired mutation within said template nucleic acid; mixing the oligonucleotide primers prepared in the previous two steps; combining said mixture in said step (d) with the template nucleic acid under conditions to allow hybridization of said oligonucleotides with said template nucleic acid, wherein said oligonucleotides are present in a concentration that is less than saturation level; extending said primers to produce a library of mutant template nucleic acids using the polymerase chain; transforming said mutant template nucleic acid from said library into a competent host cell; expressing protein corresponding to said mutant nucleic acid in said host cell; and screening said expressed proteins for desired characteristics.

DETAILED DESCRIPTION

Figure 1:
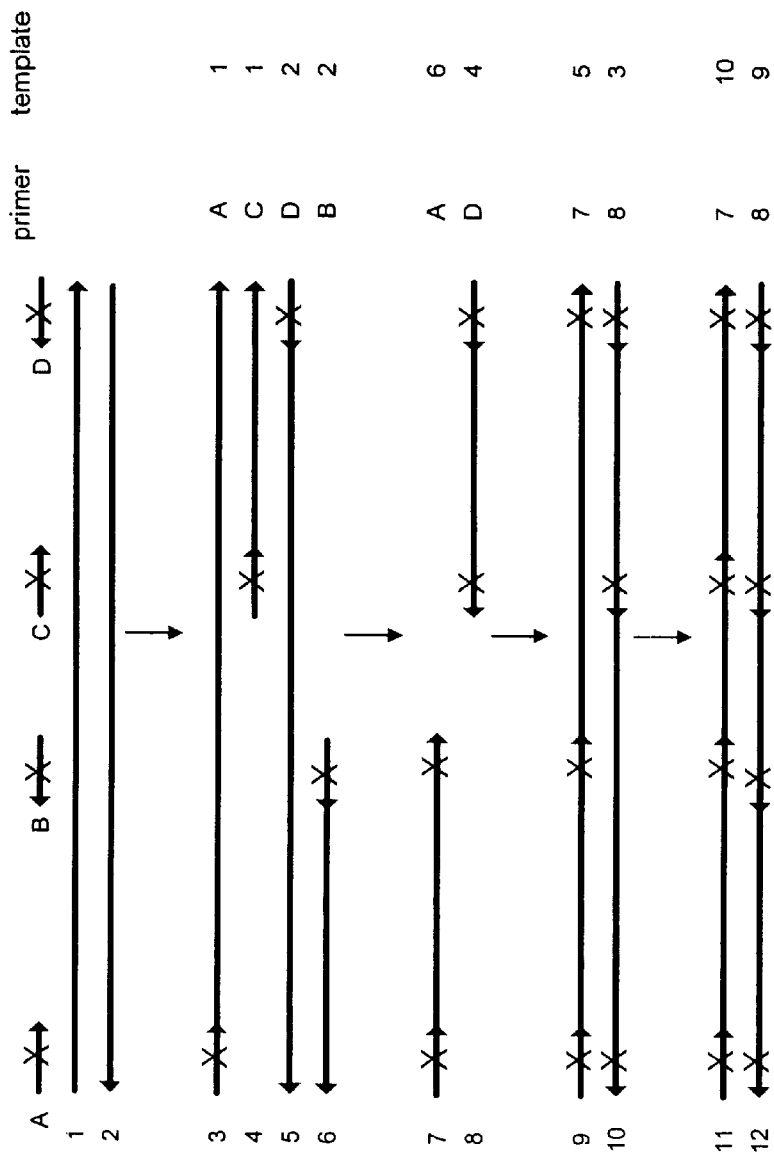
FIG. 1 illustrates a typical PCR reaction using multiple primers.

The present invention relates to methods for introducing limited but focused diversity into a nucleic acid sequence. The methods provided for herein provide for several significant levels of control that can allow the experimenter to optimize the obtained mutant library based on the specific needs for the specific experiment. For example, control over which positions of the sequence will be mutated and also which nucleotides will be varied in each of the mutagenized positions and the specific ratio of these nucleotides allows for significant and important levels of variation in a given nucleic acid library. In addition, it is possible to control the average number of mutations per clone in the resulting library.

Thus, according to the present invention, a method of producing a library of mutant nucleic acid molecules is provided comprising the steps of: (a) obtaining a template nucleic acid; (b) preparing an oligonucleotide primer pair corresponding to the ends of said said template nucleic acid; (c) preparing two mutagenic oligonucleotide primers corresponding to a first and a second desired mutation within said template nucleic acid; (d) mixing the oligonucleotide primers prepared in said steps (b) and (c); (e) combining said mixture in said step (d) with the template nucleic acid under conditions to facilitate the polymerase chain reaction, wherein said mutagenic oligonucleotides are present in a concentration that is less than saturation concentration. In a preferred embodiment, the template nucleic acid is a single nucleic acid. In another preferred embodiment of the invention, the mixture of oligonucleotide primers further includes non-mutagenic oligonucleotide primers corresponding to either or both of said first and second oligonucleotides. In a further preferred embodiment of the invention, the primers are added in a pre-defined ratio.

In another embodiment of the invention, a method of producing a library of mutant nucleic acid molecules is provided comprising the steps of: (a) obtaining a template nucleic acid; (b) preparing an oligonucleotide primer pair corresponding to the ends of said template nucleic acid; (c) preparing two mutagenic oligonucleotide primers corresponding to a first and a second desired mutation within said template nucleic acid; (d) mixing the oligonucleotide primers prepared in said steps (b) and (c); (e) combining said mixture in said step (d) with the template nucleic acid under conditions to facilitate the polymerase chain reaction, wherein said mutagenic oligonucleotides are present in a concentration that is less than saturation concentration; (f) transforming said mutant template nucleic acid from said library into a competent host cell; (g) expressing protein corresponding to said mutant nucleic acid in said host cell; and (h) screening said expressed proteins for desired characteristics. In a preferred embodiment, the mutant template nucleic acids are ligated into an appropriate vector prior to transformation to a suitable host cell.

In another preferred embodiment, in vitro expression and screening methods may be used for selection and/or screening of the mutant template nucleic acids. Such methods are known in the art and are described in, for example, Hanes, J. and A. Pluckthun (1997) *Proc. Natl. Acad. Sci. U S A* 94, 4937–42.

The term "template nucleic acid" as used herein refers to a nucleic acid for which it is desired to develop a library of related nucleic acids the members of which have altered or modified characteristics compared to the template nucleic acid and/or encode a protein which has altered or modified characteristics compared to the protein encoded by the template nucleic acid. Any source of nucleic acid, in purified or nonpurified form, can be utilized as the template nucleic acid, provided it includes the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the beta-globin gene contained in whole human DNA or a portion of nucleic acid sequence due to a particular microorganism which organism might constitute only a very minor fraction of a particular biological sample. The template nucleic acid may contain more than one desired specific nucleic acid sequence which may be the same or different. Therefore, while a preferred embodiment of the present process is for producing a library from one specific nucleic acid sequence, the present invention further has usefulness for creating variants simultaneously of more than one specific nucleic acid sequence. The nucleic acid or acids may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al, Molecular Cloning: A Laboratory Manual, (New York: Cold Spring Harbor Laboratory, 1982), pp 280–281. The present process can mutagenize any specific nucleic acid sequence. It is only necessary that a sufficient number of bases be known in sufficient detail so that at least two mutagenic oligonucleotide primers can be prepared which will hybridize to the desired sequence at desired positions along the sequence and that two oligonucleotide primers can be prepared which correspond to the opposite ends of the template nucleic acic. Using primers as described herein, an extension product synthesized from one primer, when it is separated from its template (complement), can serve as a template for extension of the other primer into a nucleic acid of defined length. The greater the knowledge about the bases at the relevant portion of the sequence, the greater can be the specificity of the primers for the target nucleic acid sequence, and thus the greater the efficiency of the process.

In a preferred embodiment, the template nucleic acid comprises either a single nucleic acid or, alternatively, a plurality of related nucleic acids. If a plurality of related nucleic acids are used, the plurality of nucleic acids may be derived from a set of natural homologs for a given nucleotide and the method of the invention comprising mixing the natural homolog template nucleic acids with mutant and, optionally, non-mutant oligonucleotide primers. It is also possible to generate mutants of a single nucleic acid which mutants are used as the plurality of template nucleic acids. In this embodiment of the invention, the inherent characteristic of PCR to recombine homologs to produce chimeric molecules is supplemented by further mutations due to the presence of the mutagenic oligonucleotides.

Alternatively, and particularly preferred, is the embodiment of the invention wherein a single nucleic acid is used as the template. In contrast to strategies comprising using a family of related nucleic acids in PCR to effect random recombination of chimeric molecules, this embodiment allows the experimenter to more precisely distribute the desired mutations in a controlled fashion. This result is possible because the inherent recombination between identical template molecules will not introduce variants. Rather, the variants in the resulting library are produced solely due to mutations contributed by the mutagenic oligonucleotide primers and by the random incorporation of nucleotides, which occurs during a typical PCR reaction. As used herein, a "single nucleic acid" means a template nucleic acid included in the reaction without significant sequence variation. While a single nucleic acid template may comprise nucleic acids of varying lengths or have minor mutant or derivative contaminants, for practical purposes the single nucleic acid used as template molecules will comprise an essentially homogeneous sequence. The presence of different length templates is considered within the definition of "single nucleic acid", e.g., shortened or truncated versions of an identical sequence may be present.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. For example, depending on the complexity of the target sequence, the oligonucleotide primer typically contains 15–25 or more nucleotides, although it may contain fewer or more nucleotides. Short primer molecules generally require cooler temperatures to form sufficiently stable hybrid complexes with template. The oligonucleotide primers of the invention may be prepared using any suitable method, such as, for example, the phosphotriester and phosphodiester methods described above, or automated embodiments thereof. In one such automated embodiment diethylphosphoramidites are used as starting materials and may be synthesized as described by Beaucage et al, Tetrahedron Letters (1981), 22:1859–1862. One method for synthesizing oligonucleotides on a modified solid support is described in U.S. Pat. No. 4,458,055. It is also possible to use a primer which has been isolated from a biological source (such as a restriction endonuclease digest).

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Typically, and preferably, however, the non-coplementary nucleotides will be in the middle of the primer. Thus, non-complementary bases or longer sequences can be interspersed into the primer, provided that the primer sequence has sufficient complementarity with the sequence of the strand to be amplified to hybridize therewith and thereby form a template for synthesis of the extension product of the other primer.

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or"non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of said mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10–50 bases in length, more preferably about 15–45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

"Contiguous mutations" means mutations which are presented within the same oligonucleotide primer. For example, contiguous mutations may be adjacent or nearby each other, however, they will be introduced into the resulting mutant template nucleic acids by the same primer.

"Discontiguous mutations" means mutations which are presented in separate oligonucleotide primers. For example, discontiguous mutations will be introduced into the resulting mutant template nucleic acids by separately prepared oligonucleotide primers.

The terms "amplification" or "amplify" or grammatical equivalents thereof, as used herein, means the production of additional copies of a nucleic acid sequence and is generally carried out using the polymerase chain reaction (PCR). PCR technologies are well known in the art (see, e.g., see Dieffenbach and Dveksler in PCR Primer, A Laboratory Manual, Cold Spring Harbor Press, Princeton, N.Y.).

The concentration of mutagenic and corresponding non-mutagenic primers is an important feature of the invention. Specifically, the invention involves using the mutagenic oligonucleotides in relatively low concentrations compared to that used in conventional PCR techniques, i.e., at "a concentration less than saturation level". By "saturation level", Applicants mean that all of the mutagenic and corresponding non-mutagenic primers will be added in limiting quantities as compared to other reaction starting products. For example, a typical PCR reaction is described in Sambrook, J., E. F. Fritsch and T. Maniatis Molecular cloning: a laboratory manual Vol. 2 pp. 14–18 [1989]. The reaction described therein uses 0.2 mM of each dNTP, resulting in a total concentration of dNTPs of 0.8 mM. Using this mixture to synthesize a product of 1 kb length requires 2000 moles of nucleotides to synthesize 1 mole of PCR product. Consequently, a reaction mixture containing 0.8 mM dNTPs can give a theoretical yield of 0.4 $\mu$M of PCR product. In practice, the yield will be substantially lower because a fraction of the dNTPs are hydrolyzed during the reaction and other side reactions will take up nucleotides. In addition other factors such as buffer capacity and enzyme activity limit the yield of a PCR reaction. In this example the Author uses primers at concentrations of 1 $\mu$M. One of each primer molecules is required for the formation of one molecule of PCR product. Consequently, this concentration of primers leads to a theoretical yield of 1 $\mu$M of PCR product, a quantity which is substantially higher than the theoretical yield based on the concentration of dNTPs. Thus, a typical PCR reaction involves the use of primers in significantly greater concentration in relation to the utilized dNTPs with a result that the primers are not completely used up during the reaction. For these reasons, it is an important feature of the invention to use primers in relatively low concentrations to ensure that the primers are exhausted in the ensuing PCR reaction. In this manner, substantially all of the added primers are incorporated into PCR products prior to other components of the reaction mixture become limiting.

The optimal concentration of the mixture of primers with respect to dNTP and template concentrations will often depend on the specific reaction conditions but can be determined using routine experimentation well within the skill of the average technician in the field. For example, such optimal concentration may be determined experimentally by performing a series of parallel reactions using different concentrations of the primer mixture. Typically, the optimal primer concentration will be in a range such that product concentration is high enough to be detected by an agarose gel but that adding higher concentrations of primer mixture leads to higher concentrations of products, establishing that primer concentration is the limiting factor in the reaction. It has been the experience of Applicants herein, for example, that a concentration of dNTPs of 0.2 mM will dictate a total concentration of primers in the range of 0.01 to 0.2 $\mu$M using otherwise standard PCR conditions such as described in Sambrook et al, supra. However, the present invention is not confined to absolute concentrations and variations are possible resulting from the specifics of the PCR reaction conditions and their effect on the component reagents in the reaction. Instead, in the present invention, a "less than saturation concentration" means that the oligonucleotide primers which are contributing to the combinatorial mutagenesis scheme are exhausted during the PCR reaction.

The PCR process is well known in the art and is described in, for example, U.S. Pat. Nos. 4,965,188; 4,683,195; 4,683, 195; 5,968,730; 5,066,584; and 4,683,202. The following descriptions of the PCR reaction are for illustrative purposes so as to better understand the use of the present invention and are not intended to be limiting regarding the variety of techniques that can be used in connection with the present invention. As known by those in the art, the PCR process can employ the thermostable polymerase described in U.S. Pat. No. 4,889,818. In general, the present invention involves the use if the polymerase chain reaction for producing mutant nucleotide libraries. In the polymerase chain reaction as used in the present invention, reaction product is produced in exponential quantities relative to the number of reaction steps involved with respect to at least one specific nucleic acid sequence given (a) that the ends of the required sequence are known in sufficient detail that oligonucleotides can be synthesized which will hybridize to them, and (b) that at least enough sequence corresponding to the mutagenic oligonucleotide primers is available. The product of the chain reaction will be a discrete nucleic acid duplex with termini corresponding to the ends of the specific primers employed.

The specific nucleic acid sequence library is produced by using the nucleic acid template. If the nucleic acid template contains two strands, it is necessary to separate the strands of the nucleic acid before it can be used as the template, either as a separate step or simultaneously with the synthesis of the primer extension products. Strand separation can be accomplished by any suitable denaturing method including physical, chemical or enzymatic means. One physical method of separating the strands of the nucleic acid involves heating the nucleic acid until it is completely (>99%) denatured. Typical heat denaturation may involve temperature ranging from about 80 deg C. to 105 deg C. for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al, "DNA Helicases", pp. 63–67, and techniques for using RecA are reviewed in C. Radding, Ann. Rev. Genetics, 16:405–37 (1982).

If the original nucleic acid containing the sequence to be mutagenized and amplified is single stranded, its complement is synthesized by adding one or two oligonucleotide primers thereto. If an appropriate single primer is added, a primer extension product is synthesized in the presence of the primer, an agent for apolymerization and the four nucleotides described below. The product will be partially complementary to the single-stranded nucleic acid and will hybridize with the nucleic acid strand to form a duplex of unequal length strands that may then be separated into single strands as described above to produce two single separated complementary strands. Alternatively, two appropriate primers may be added to the single-stranded nucleic acid and the reaction carried out. In the present invention, it is preferred to nest the mutagenic primers inside of another set of primers which correspond to the end of the template. For example, one set of primers which are not intended to introduce mutations are designed to correspond to the 5' and 3' ends of the template, and mutagenic primers or mixed mutagenic and non-mutagenic primers are designed which are complementary to sequence between the two end primers.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for mutagenesis and the synthesis of additional nucleic acid strands. This synthesis can be performed using any suitable method. Generally it occurs in a buffered aqueous solution, preferably at a pH of 7–9, most preferably about 8. Primers exist in a less than saturation concentration.

The deoxyribonucleoside triphosphates dATP, dCTP, dGTP and dTTP are also added to the synthesis mixture in adequate amounts and the resulting solution is heated to about 90 deg–100 deg C. for from about 10 seconds to 10 minutes, preferably from 1 to 4 minutes. After this heating period the solution is allowed to cool to from 20 deg C.–40 deg C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heatstable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

PCR as used in the present invention can be performed in a step-wise fashion where after each step new reagents are added, or simultaneously, where all reagents are added at the initial step, or partially step-wise and partially simultaneous, where fresh reagent is added after a given number of steps. If a method of strand separation, such as heat, is employed which will inactivate the agent for polymerization, as in the case of a heat-labile enzyme, then it is necessary to replenish the agent for polymerization after every strand separation step. The simultaneous method may be utilized when a number of purified components, including an enzymatic means such as helicase, is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as rATP, the four nucleotides, the oligonucleotide primers in molar excess, and the inducing agent, e.g., Klenow fragment of E. coli DNA polymerase I. If heat is used for denaturation in a simultaneous process, a heat-stable inducing agent such as a thermostable polymerase may be employed which will operate at an elevated temperature, preferably 65 deg C.–90 deg C. depending on the inducing agent, at which temperature the nucleic acid will consist of single and double strands in equilibrium. For smaller lengths of nucleic acid, lower temperatures of about 50 deg C. may be employed. The upper temperature will depend on the temperature at which the enzyme will degrade or the temperature above which an insufficient level of primer hybridization will occur. Such a heat-stable enzyme is described, e.g., by A. S. Kaledin et al, Biokhimiya, 45, 644–651 (1980). Each step of the process will occur sequentially notwithstanding the initial presence of all the reagents. Additional materials may be added as necessary. After the appropriate length of time has passed to produce the desired amount of the specific nucleic acid sequence, the reaction may be halted by inactivating the enzymes in any known manner or separating the components of the reaction.

The exponential nature of the PCR reaction is demonstrated as follows. Double-stranded DNA containing the desired sequence comprised of complementary strands and is utilized as the nucleic acid. During the first and each subsequent reaction cycle extension of each oligonucleotide primer on the original template will produce one new ssDNA molecule product of indefinite length which terminates with only one of the primers. These products, hereafter referred to as "long products" or "megaprimers," will accumulate in a linear fashion; that is, the amount present after any number of cycles will be proportional to the number of cycles.

The long products thus produced will act as templates for one or the other of the oligonucleotide primers during subsequent cycles and will produce molecules of the desired sequence. These molecules will also function as templates for one or the other of the oligonucleotide primers, producing further desired product and thus a chain reaction can be sustained which will result in the accumulation of desired product at an exponential rate relative to the number of cycles.

By-products formed by oligonucleotide hybridizations other than those intended are not self-catalytic (except in rare instances) and thus accumulate at a linear rate.

The steps of this process can be repeated indefinitely, being limited only by the amount of primers, the agent for polymerization (polymerase) and nucleotides present. The amount of original nucleic acid remains constant in the entire process, because it it not replicated. The amount of the long products increases linearly because they are produced only from the original nucleic acid. The amount of the specific sequence increases exponentially. Thus, the specific sequence will become the predominant species. This is illustrated in the following table, which indicates the relative amounts of the species theoretically present after n cycles, assuming 100% efficiency at each cycle:

TABLE 1

NUMBER OF STRANDS AFTER 0–n CYCLES

| CYCLE NUMBER | TEMPLATE | LONG PRODUCTS | SPECIFIC SEQUENCE |
|---|---|---|---|
| 0 | 1 | — | — |
| 1 | 1 | 1 | 0 |
| 2 | 1 | 2 | 1 |
| 3 | 1 | 3 | 4 |
| 5 | 1 | 5 | 26 |
| 10 | 1 | 10 | 1013 |
| 15 | 1 | 15 | 32,752 |
| 20 | 1 | 20 | 1,048,555 |
| n | 1 | n | $(2^{<n>} - n - 1)$ |

When a single-stranded nucleic acid is utilized as the template, only one long product is formed per cycle.

The invention described herein requires that the PCR reaction proceed with multiple primers. This allows for many reactions to occur in parallel. While the reaction continues for each of the many primers, there exist certain factors which cause a bias towards one or more of the primer-initiated reactions as compared to other primer-initiated reactions. For example, the concentration of the different oligonucleotide primers, the efficiency and specific kinetics of hybridization between one oligonucleotide primer vis-a-vis another oligonucleotide primer, the concentration of free nucleotide and/or polymerase, and the reaction conditions will all effect the degree to which certain oligonucleotide primers are favored in the PCR reaction over others. As an example, reactions involving relatively short and highly complementary oligonucleotide primers, as opposed to megaprimer or long product reactions involving relatively longer and less complementary oligonucleotide primers, are favored. Furthermore, reactions which will lead to the formation of relatively short sequences are generally favored over reactions which lead to the formation of longer products. The magnitude of the favored reaction is significantly increased by the fact that PCR, during initial cycles, leads to an exponential amplification or reaction products. If one particular pair of primers has measurably greater efficiency in terms of reaction kinetics, amplification of that primer pair over other pairs of primers in the mixture will rapidly dominate in the reaction mixture. As a result, exponential amplification of even small differences in reaction rate can lead to dramatically different product ratios. In the context of producing combinatorial libraries, the resulting product ratio discrepancies forces a reaction product bias which will result in a failure to develop a representative library of nucleotide template mutants.

Figure 2:
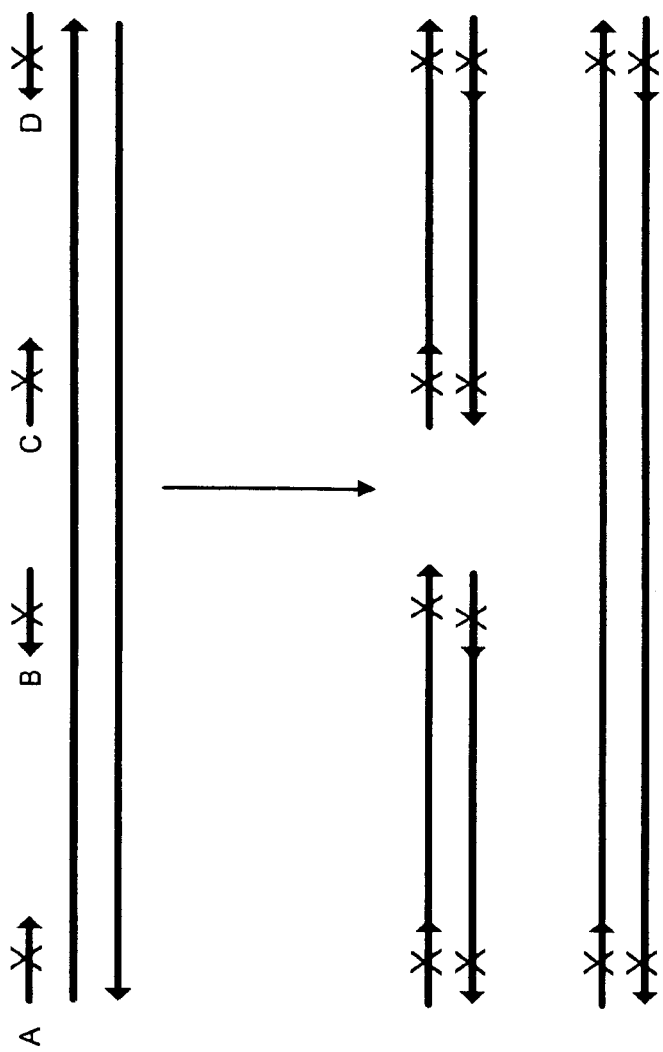
FIG. 2 illustrates a PCR reaction using the same primers as in FIG. 2 but assuming no recombination (no megapriming). If all reactions would occur with identical rate then one would expect to obtain a mixture of three products all containing primer sequences at their ends. In reality the rate of formation of these three products will depend on many parameters. Usually, the formation of short products will be favored over the formation of full length sequences and one or both of the shorter products would be expected to dominate the product mixture.

The formation of sequences which contain internal primer sequences like sequences 9–12 in FIG. 1 requires annealing between intermediate products (long product or megaprimers) which have formed during previous cycles of the reaction. An example is the formation of sequence 9 in FIG. 1 which requires the annealing between sequence 7 and sequence 5. Reactions involving megaprimers (i.e., long products) can only occur during latter cycles of the reaction and one would expect their products to be rare in the final product mixture. By contrast, FIG. 2 shows PCR products which can be formed if, instead of megapriming, it is a particular combination of primers which controls the reaction products obtained.

In the method of the invention, relatively low concentrations of oligonucleotide primers are used compared to standard PCR techniques. If a particular primer can react very efficiently during early cycles of PCR then it will be rapidly depleted from the reaction mixture. As a result, reactions that involve primers with favorable reaction kinetics will slow down during latter cycles of the reaction. As a consequence other reactions that involve less efficient reaction kinetics or megaprimers will dominate during latter cycles of PCR. Thus, using primers in relatively low concentrations results in a relatively uniform distribution of mutations in the resulting library and favors the formation of long sequences containing more then two oligo-derived mutations.

During a PCR reaction, the conditions are constantly changing leading ultimately to a stop of DNA amplification. For instance, trinucleotides and primers get depleted, the pH can change,or the DNA polymerase may lose activity. For the current invention it is important that the added mutagenic and non-mutagenic oligonucleotides are substantially depleted before other reaction parameters terminate the progress of DNA amplification. Thus, the oligonucleotide primers must be added in less than a saturation concentration.

Conditions which allow a primer to extend on a template generally include a polymerase, nucleotides and a suitable buffer. Polymerases for use in PCR can be either thermostable or non-stable polymerase enzymes. Preferably the polymerase used is a thermostable polymerase such as the Pfu DNA polymerase (Stratagene). The Taq polymerase, phage T7 polymerase, phage T4 polymerase, DNA polymerase I and other known polymerases known in the art which are useful in primer extension may also be used advantageously. When the DNA molecule for mutagenesis is relatively long, such as entire operons or large genes, it is useful to use a mixture of thermostable DNA polymerases, wherein one of the DNA polymerases has 5'-3' exonuclease activity and the other DNA polymerase lacks 5'-3' exonuclease activity. A description of how to amplify long regions of DNA using these polymerase mixtures can be found in, among other places, U.S. Pat. No. 5,436,149.

Thus, in one embodiment, at least one template fragment is reacted with a plurality of primers under conditions suitable for extension of said primers, wherein said plurality of primers comprise wild type and mutagenic primers, at least one of which wild type primers corresponds to a mutagenc primer in terms of locus of hybridization on the nucleic acid template. Preferably the extension cycle or round is repeated at least 2 times, more preferably up to 5 times, more preferably up to 10 times, and most preferably up to 100 times or more. The cycles of assembly, denaturation and reassembly are reiterated for a sufficient time to generate full-length gene.

In one embodiment, protein products encoded by nucleic acids in the library generated according to the invention retain their function as in the wild type protein, such as catalytic activity, but have an altered property with respect to some desired characteristic. Generally, the methods of the invention are useful for the generation of novel mutant nucleic acid libraries. The mutant nucleic acids may encode useful proteins, such as novel receptors, ligands, antibodies and enzymes. These mutant nucleic acids may also comprise untranslated regions of genes, untranslated regions of genes, introns, exons, promoter regions, enhancer regions terminator regions, recognition sequences and other regulatory sequences for gene expression.

Thus, the methods of the invention provide for the formation of mutant nucleic acids ranging from 50–100 bp to several Mbp. The mutant nucleic acid library of the invention may be cloned into vector, propagated and screened for a species or first subpopulation with a desired property. This results in the identification and isolation of, or enrichment for, mutant nucleic acids encoding polypeptides that have acquired a desired property.

The mutant nucleic acids from the library may be further subjected to assays which screen for desired characteristics in the nucleic acid or in a polypeptide encoded by the nucleic acid. Additionally, the mutant nucleic acid may be cloned into a vector at any time after generation of the mutant template nucleic acid library. As outlined above, the invention provides mutant nucleic acid libraries, wherein said nucleic acids encode polypeptides. The library of mutant nucleic acids will encode at least one polypeptide which has at least one property which is different from the same property of the corresponding sequence or corresponding naturally occurring polypeptide. The properties described herein may also be referred to as biological activities.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, Km, kcat, Kcat/km ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

A change in substrate specificity is defined as a difference between the kcat/Km ratio of the precursor protein and that of the variant thereof. The kcat/Km ratio is generally a measure of catalytic efficiency. Generally, the objective will be to generate variants of precursor proteins with greater (numerically large) kcat/Km ratio for a given substrate when compared to that of the naturally occurring protein, thereby enabling the use of the protein to more efficiently act on a target substrate. However, it may be desirable to decrease efficiency. An increase in kcat/Km ratio for one substrate may be accompanied by a reduction in kcat/Km ratio for another substrate. This is a shift in substrate specificity and variants of naturally occurring proteins exhibiting such shifts have utility where the naturally occurring protein is undesirable, e.g., to prevent undesired hydrolysis of a particular substrate in an admixture of substrates. Km and kcat are measured in accordance with known procedures.

A change in oxidative stability is evidenced by at least about 10% or 20%, more preferably at least 50% increase of enzyme activity when exposed to various oxidizing conditions. Such oxidizing conditions include, but are not limited to exposure of the protein to the organic oxidant diperdodecanoic acid (DPDA). Oxidative stability is measured by known procedures.

A change in alkaline stability is evidenced by at least about a 5% or greater increase or decrease (preferably increase) in the half life of the enzymatic activity of a variant of a naturally occurring protein when compared to that of the naturally occurring protein. In the case of e.g., subtilisins, alkaline stability can be measured as a function of autoproteolytic degradation of subtilisin at alkaline pH, e.g., 0.1M sodium phosphate, pH 12 at 25° C. or 30° C. Generally, alkaline stability is measured by known procedures.

A change in thermal stability is evidenced by at least about a 5% or greater increase or decrease (preferably increase) in the half life of the catalytic activity of a variant of naturally occurring protein when exposed to a relatively high temperature and neutral pH as compared to that of the naturally occurring protein. In the case of e.g., subtilisins, thermal stability can be measured as a function of autoproteolytic degradation of subtilisin at elevated temperatures and neutral pH, e.g., 2 mM calcium chloride, 50 mM MOPS, pH 7.0 at 59° C. Generally, thermal stability is measured by known procedures.

Receptor variants, for example are experimentally tested and validated in in vivo and in in vitro assays. Suitable assays include, but are not limited to, e.g., examining their binding affinity to natural ligands and to high affinity agonists and/or antagonists. In addition to cell-free biochemical affinity tests, quantitative comparisons are made comparing kinetic and equilibrium binding constants for the natural ligand to the naturally occurring receptor and to the receptor variants. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. For most receptors described herein, the binding constant between a natural ligand and its corresponding naturally occurring receptor is well documented in the literature. Comparisons with the corresponding naturally occurring receptors are made in order to evaluate the sensitivity and specificity of the receptor variants. Preferably, binding affinity to natural ligands and agonists is expected to increase relative to the naturally occurring receptor, while antagonist affinity should decrease. Receptor variants with higher affinity to antagonists relative to the non-naturally occurring receptors may also be generated by the methods of the invention.

Similarly, ligand variants, for example, are experimentally tested and validated in in vivo and in in vitro assays. Suitable assays include, but are not limited to, e.g., examining their binding affinity to natural receptors and to high affinity agonists and/or antagonists. In addition to cell-free biochemical affinity tests, quantitative comparison is made comparing kinetic and equilibrium binding constants for the natural receptor to the naturally occurring ligand and to the ligand variants. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. For most ligands described herein, the binding constant between a natural receptor and its corresponding naturally occurring ligand is well documented in the literature. Comparisons with the corresponding naturally occurring ligands are made in order to evaluate the sensitivity and specificity of the ligand variants. Preferably, binding affinity to natural receptors and agonists is expected to increase relative to the naturally occurring ligand, while antagonist affinity should decrease. Ligand variants with higher affinity to antagonists relative to the non-naturally occurring ligands may also be generated by the methods of the invention.

By "protein" herein is meant at least two covalently attached amino acids, which may include proteins, polypeptides, oligopeptides and peptides. The protein may be a naturally occurring protein, a variant of a naturally occurring protein or a synthetic protein. The protein may be made up of naturally occurring amino acids and peptide bonds, or synthetic peptidomimetic structures, generally depending on the method of synthesis. Thus "amino acid", in one embodiment, means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. Stereoisomers of the twenty conventional amino acids, unnatural amino acids such as a,a-disubstituted amino acids, N-alkyl amino acids, lactic acid, and other unconventional amino acids may also be suitable components for proteins of the present invention. Examples of unconventional amino acids include, but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids. If non-naturally occurring side chains are used, non-amino acid substituents may be used, for example to prevent or retard in vivo degradations. Proteins including non-naturally occurring amino acids may be synthesized or in some cases, made by recombinant methods; see van Hest et al., FEBS Lett. 428:(1–2) 68–70 (1998); and Tang et al., Abstr. Pap. Am. Chem. S218:U138-U138 Part 2 (1999), both of which are expressly incorporated by reference herein. Included within this definition are proteins whose amino acid sequence is altered by one or more amino acids when compared to the sequence of a naturally occurring or precursor protein.

A "variant protein" as used herein means a protein which is altered from a precursor protein. In the context of the present invention, this means that the nucleic acid template is modified, through the use of the presently described invention, in such a way that the protein expressed thereby is changed in terms of sequence. Thus, by using the present invention, a library of mutant nucleic acids is developed from the template nucleic acid(s) and this library is subsequently cloned and screened for expressed protein activities to detect useful variant proteins. Generally, this means that the protein has modified properties in some manner.

The nucleic acids may be from any number of eukaryotic or prokaryotic organisms or from archaebacteria. Nucleic acids from mammals include, but are not limited to, rodents (rats, mice, hamsters, guinea pigs, etc.), primates, farm animals (including sheep, goats, pigs, cows, horses, etc) and humans. Other suitable examples of eukaryotic organisms include plant cells, such as maize, rice, wheat, cotton, soybean, sugarcane, tobacco, and arabidopsis; fish, algae, yeast, such as *Saccharomyces cerevisiae;* Aspergillus, Trichoderma, Penicillium, Fusarium and other filamentous fungi; and tissue culture cells from avian or mammalian origins. Also preferred are nucleic acids from prokaryotic organisms. Suitable examples of prokaryotic organisms include gram negative organisms and gram positive organisms. Specifically included are enterobacteriaciae bacteria, pseudomonas, micrococcus, corynebacteria, bacillus, lactobacilli, streptomyces, and agrobacterium. Polynucleotides encoding proteins and enzymes isolated from extremophilic organisms, includining, but not limited to hyperthermophiles, psychrophiles, psychrotrophs, halophiles, barophiles and acidophiles, are useful sources of nucleic acids. Such enzymes may function at temperatures above 100° C. in terrestrial hot springs and deep sea thermal vents, at temperatures below 0° C. in arctic waters, in the saturated salt environment of the Dead Sea, at pH values at around 0 in coal deposits and geothermal sulfur-rich rich springs, or at pH values greater than 11 in sewage sludge.

The proteins can be intracellular proteins, extracellular proteins, secreted proteins, enzymes, ligands, receptors, antibodies or portions thereof.

The template nucleic acid may encode all or a portion of an enzyme. By "enzyme" herein is meant any of a group of proteins that catalyzes a chemical reaction. Enzymes include, but are not limited to (i) oxidoreductases; (ii) transferases, comprising transferase transferring one-carbon groups (e.g., methyltransferases, hydroxymethyl-, formyl-, and related transferases, carboxyl- and carbamoyltransferases, amidinotransferases) transferases transferring aldehydic or ketonic residues, acyltransferases (e.g., acyltransferases, aminoacyltransferas), glycosyltransferases (e.g., hexosyltransferases, pentosyltransferases), transferases transferring alkyl or related groups, transferases transferring nitrogenous groups (e.g., aminotransferases, oximinotransferases), transferases transferring phosphorus-containing groups (e.g., phosphotransferases, pyrophosphotransferases, nucleotidyltransferases), transferases transferring sulfur-containing groups (e.g., sulfurtransferases, sulfotransferases, CoA-transferases), (iii) Hydrolases comprising hydrolases acting on ester bonds (e.g., carboxylic ester hydrolases, thioester hydrolases, phosphoric monoester hydrolases, phosphoric diester hydrolases, triphosphoric monoester hydrolases, sulfuric ester hydrolases), hydrolases acting on glycosyl compounds (e.g., glycoside hydrolases, hydrolyzing N-glycosyl compounds, hydrolyzing S-glycosyl compound), hydrolases acting on ether bonds (e.g., thioether hydrolases), hydrolases acting on peptide bonds (e.g., α-aminoacylpeptide hydrolases, peptidyl-amino acid hydrolases, dipeptide hydrolases, peptidyl-peptide hydrolases), hydrolases acting on C—N bonds other than peptide bonds, hydrolases acting on acid-anhydride bonds, hydrolases acting on C—C bonds, hydrolases acting on halide bonds, hydrolases acting on P—N bonds, (iv) lyases comprising carbon-carbon lyases (e.g., carboxy-lyases, aldehyde-lyases, ketoacid-lyases), carbon-oxygen lyases (e.g., hydro-lyases, other carbon-oxygen lyases), carbon-nitrogen lyases (e.g., ammonia-lyases, amidine-lyases), carbon-sulfur sulfur lyases, carbon-halide lyases, other lyases, (v) isomerases comprising racemases and epimerases, cis-trans isomerases, intramolecular oxidoreductases, intramolecular transferases, intramolecular lyases, other isomerases, (vi) ligases or synthetases comprising ligases or synthetases forming C—O bonds, forming C—S bonds, forming C—N bonds, forming C—C bonds.

Carbonyl hydrolases are enzymes that hydrolyze compounds comprising O=C—X bonds, wherein X is oxygen or nitrogen. They include hydrolases, e.g., lipases and peptide hydrolases, e.g., subtilisins or metalloproteases. Peptide hydrolases include α-aminoacylpeptide hydrolase, peptidylamino-acid hydrolase, acylamino hydrolase, serine carboxypeptidase, metallocarboxy-peptidase, thiol proteinase, carboxylproteinase and metalloproteinase. Serine, metallo, thiol and acid proteases are included, as well as endo and exo-proteases.

In another embodiment of the invention, the template nucleic acid encodes all or a portion of a receptor. By "receptor" or grammatical equivalents herein is meant a proteinaceous molecule that has an affinity for a ligand. Examples of receptors include, but are not limited to antibodies, cell membrane receptors, complex carbohydrates and glycoproteins, enzymes, and hormone receptors.

Cell-surface receptors appear to fall into two general classes: type 1 and type 2 receptors. Type 1 receptors have generally two identical subunits associated together, either covalently or otherwise. They are essentially preformed dimers, even in the absence of ligand. The type 1 receptors include the insulin receptor and the IGF (insulin like growth factor) receptor. The type-2 receptors, however, generally are in a monomeric form, and rely on binding of one ligand to each of two or more monomers, resulting in receptor oligomerization and receptor activation. Type-2 receptors include the growth hormone receptor, the leptin receptor, the LDL (low density lipoprotein) receptor, the GCSF (granulocyte colony stimulating factor) receptor, the interleukin receptors including IL-1, IL-2, IL-3, IL-4, IL-5, IL-6, IL-7, IL-8, IL-9, IL-11, IL-12, IL-13, IL-15, IL-17, ect., receptors, EGF (epidermal growth factor) receptor, EPO (erythropoietin) receptor, TPO (thrombopoietin) receptor, VEGF (vascular endothelial growth factor) receptor, PDGF (platelet derived growth factor; A chain and B chain) receptor, FGF (basic fibroblast growth factor) receptor, T-cell receptor, transferrin receptor, prolactin receptor, CNF (ciliary neurotrophic factor) receptor, TNF (tumor necrosis factor) receptor, Fas receptor, NGF (nerve growth factor) receptor, GM-CSF (granulocyte/macrophage colony stimulating factor) receptor, HGF (hepatocyte growth factor) receptor, LIF (leukemia inhibitory factor), TGFα/β (transforming growth factor α/β) receptor, MCP (monocyte chemoattractant protein) receptor and interferon receptors (α, β and γ). Further included are T cell receptors, MHC (major histocompatibility antigen) class I and class II receptors and receptors to the naturally occurring ligands, listed below.

In one embodiment of the invention, the template nucleic acid encodes all or a portion of a ligand. By "ligand" or grammatical equivalents herein is meant a proteinaceous molecule capable of binding to a receptor. Ligands include, but are not limited to cytokines IL-1ra, IL-1, IL-1a, IL-1b, IL-2, IL-3, IL-4, IL-5, IL-6, IL-8, IL-10, IFN-β, INF-γ, IFN-α-2a; IFN-α-2B, TNF-α; CD40 ligand (chk), human obesity protein leptin, GCSF, BMP-7, CNF, GM-CSF, MCP-1, macrophage migration inhibitory factor, human glycosylation-inhibiting factor, human rantes, human macrophage inflammatory protein 1β, hGH, LIF, human melanoma growth stimulatory activity, neutrophil activating peptide-2, CC-chemokine MCP-3, platelet factor M2, neutrophil activating peptide 2, eotaxin, stromal cell-derived factor-1, insulin, IGF-I, IGF-II, TGF-β1, TGF-β2, TGF-β3, TGF-α, VEGF, acidic-FGF, basic-FGF, EGF, NGF, BDNF (brain derived neurotrophic factor), CNF, PDGF, HGF, GCDNF (glial cell-derived neurotrophic factor), EPO, other extracellular signaling moieties, including, but not limited to, hedgehog Sonic, hedgehog Desert, hedgehog Indian, hCG; coagulation factors including, but not limited to, TPA and Factor VIIa.

In one embodiment of the invention, the template nucleic acid encodes all or a portion of an antibody. The term "antibody" or grammatical equivalents, as used herein, refer to antibodies and antibody fragments that retain the ability to bind to the epitope that the intact antibody binds and include polyclonal antibodies, monoclonal antibodies, chimeric antibodies, anti-idiotype (anti-ID) antibodies. Preferably, the antibodies are monoclonal antibodies. Antibody fragments include, but are not limited to the complementarity-determining regions (CDRs), single-chain fragment variables (scfv), heavy chain variable region (VH), light chain variable region (VL).

Information with respect to nucleic acid sequences and amino acid sequences for enzymes, receptors, ligands, and antibodies is readily available from numerous publications and several data bases, such as the one from the National Center for Biotechnology Information (NCBI).

Variant proteins of the present invention are selected by screening. Such screening can be performed by cloning the nucleic acids from the library into suitable host cells. Generally, screening requires the insertion of the mutant nucleic acids produced hereby into vectors and the cloning of such vectors into a suitable host cell for expression of protein which can be assayed. A discussion follows which is pertinent to the development of clones host cells which can be used for screeing variant proteins for useful properties, or alternatively, for expressing a selected nucleic acid which is developed using the methods described herein and isolated as a preferred nucleic acid for producing desirable proteins.

Using the mutant nucleic acids of the present invention which encode variant proteins, a variety of expression vectors may be made. The expression vectors may be either self-replicating extrachromosomal vectors or vectors which integrate into a host genome. Generally, these expression vectors include transcriptional and translational regulatory nucleic acid operably linked to the nucleic acid encoding the variant protein. The term "control sequence" or grammatical equivalents thereof, as used herein, refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize polyadenylation signals and enhancers. In one embodiment of the invention the control sequences are generated by using the methods described herein.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading frame. However, enhancers do not have to be contiguous. Linking is accomplished by ligation at convenient restriction sites. If such sites do not exist, synthetic oligonucleotide adaptors, linkers or recombination methods are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells. In one embodiment of the invention the control sequences are operably linked to a another nucleic acid by using the methods described herein.

In a preferred embodiment, when a naturally occurring secretory sequence leads to a low level of secretion of a variant protein, a replacement of the naturally occurring secretory leader sequence is desired. In this embodiment, an unrelated secretory leader sequence is operably linked to a variant protein encoding nucleic acid leading to increased protein secretion. Thus, any secretory leader sequence resulting in enhanced secretion of the variant protein, when compared to the secretion of the naturally occurring protein and its secretory sequence, is desired. Suitable secretory leader sequences that lead to the secretion of a protein are know in the art. In another preferred embodiment, a secretory leader sequence of a naturally occurring protein or a variant protein is removed by techniques known in the art and subsequent expression results in intracellular accumulation of the expressed protein.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the STAT or CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art. In addition, in a preferred embodiment, the expression vector contains a selectable marker gene to allow the selection of transformed host cells. Selection genes are well known in the art and will vary with the host cell used.

The nucleic acids are introduced into the cells, either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The nucleic acids may stably integrate into the genome of the host cell, or may exist either transiently or stably in the cytoplasm (i.e. through the use of traditional plasmids, utilizing standard regulatory sequences, selection markers, etc.).

The proteins of the present invention are produced by culturing a host cell transformed either with an expression vector containing nucleic acid encoding the protein or with the nucleic acid encoding the protein alone, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculovirus used in insect cell expression systems is a lytic virus, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli,* Bacillus, SF9 cells, C129 cells, 293 cells, Neurospora, Trichoderma, Aspergillus, Fusarium, Streptomyces, BHK, CHO, COS, *Pichia pastoris,* etc.

In one embodiment, the proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen can be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable mammalian cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. See the ATCC cell line catalog, hereby expressly incorporated by reference.

In one embodiment, the cells may be additionally genetically engineered, that is, they contain exogenous nucleic acid other than the mutant nucleic acids of the invention.

In a preferred embodiment, the proteins are expressed in bacterial systems. Bacterial expression systems are well known in the art. A suitable bacterial promoter is any nucleic acid sequence capable of binding bacterial RNA polymerase and initiating the downstream (3') transcription of the coding sequence of the protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the expressed protein in bacteria. The signal sequence typically encodes a signal peptide comprised of hydrophobic amino acids, which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to the mutant nucleic acid, are preferred.

In a preferred embodiment, the proteins of the invention are expressed in bacteria and/or are displayed on the bacterial surface. Suitable bacterial expression and display systems are known in the art [Stahl and Uhlen, Trends Biotechnol. 15:185–92 (1997); Georgiou et al., Nat. Biotechnol. 15:29–34 (1997); Lu et al., Biotechnology 13:366–72 (1995); Jung et al., Nat. Biotechnol. 16:576–80 (1998)].

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, proteins are produced in insect cells. Expression vectors for the transformation of insect cells, and in particular, baculovirus-based expression vectors, are well known in the art.

In another preferred embodiment, proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, the proteins of the invention are expressed in yeast and/or are displayed on the yeast surface. Suitable yeast expression and display systems are known in the art (Boder and Wittrup, Nat. Biotechnol. 15:553–7 (1997); Cho et al., J. Immunol. Methods 220:179–88 (1998); all of which are expressly incorporated by reference). Surface display in the ciliate *Tetrahymena thermophila* is described by Gaertig et al. Nat. Biotechnol. 17:462–465 (1999), expressly incorporated by reference.

In one embodiment, proteins are produced in viruses and/or are displayed on the surface of the viruses. Expression vectors for protein expression in viruses and for display, are well known in the art and commercially available (see review by Felici et al., Biotechnol. Annu. Rev. 1:149–83 (1995)). Examples include, but are not limited to M13 (Lowman et al., (1991) Biochemistry 30:10832–10838 (1991); Matthews and Wells, (1993) Science 260:1113–1117; Stratagene); fd (Krebber et al., (1995) FEBS Lett. 377:227–231); T7 (Novagen, Inc.); T4 (Jiang et al., Infect. Immun. 65:4770–7 (1997); lambda (Stolz et al., FEBS Lett. 440:213–7 (1998)); tomato bushy stunt virus (Joelson et al., J. Gen. Virol. 78:1213–7 (1997)); retroviruses (Buchholz et al., Nat. Biotechnol. 16:951–4 (1998)). All of the above references are expressly incorporated by reference. In another embodiment the proteins of the invention are produced in vitro, as in, for example, Patnaik, R. et al., (1998) *Biotechniques* 24, 862–868.

In addition, the proteins of the invention may be further fused to other proteins, if desired, for example to increase expression or increase stability. Once made, the proteins may be covalently modified. One type of covalent modification includes reacting targeted amino acid residues of a protein with an organic derivatizing agent that is capable of reacting with selected side chains or the N- or C-terminal residues of a protein. Derivatization with bifunctional agents is useful, for instance, for crosslinking a protein to a water-insoluble support matrix or surface for use in the method for purifying anti-protein antibodies or screening assays, as is more fully described below. Commonly used crosslinking agents include, e.g., 1,1-bis(diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the protein included within the scope of this invention comprises altering the native glycosylation pattern of the variant protein or of the corresponding naturally occurring protein. "Altering the native glycosylation pattern" is intended for purposes herein to mean deleting one or more carbohydrate moieties found in a protein, and/or adding one or more glycosylation sites that are not present in the respective protein.

Addition of glycosylation sites to a protein may be accomplished by altering the amino acid sequence thereof. The alteration may be made, for example, by the addition of, or substitution by, one or more serine or threonine residues to the protein (for O-linked glycosylation sites). The amino acid sequence may optionally be altered through changes at the DNA level, particularly by mutating the DNA encoding the protein at preselected bases such that codons are generated that will translate into the desired amino acids.

Another means of increasing the number of carbohydrate moieties on the protein is by chemical or enzymatic coupling of glycosides to the polypeptide. Such methods are described in the art, e.g., in WO 87/05330, published Sep. 11, 1987 and in Aplin and Wriston, CRC Crit. Rev. Biochem., pp. 259–306 (1981).

Removal of carbohydrate moieties present on the protein may be accomplished chemically or enzymatically or by mutational substitution of codons encoding for amino acid residues that serve as targets for glycosylation. Chemical deglycosylation techniques are known in the art and described, for instance, by Hakimuddin et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of a protein comprises linking the protein to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In a preferred embodiment, the protein is purified or isolated after expression. The proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification may be necessary.

Alternatively, it is possible to isolate variant nucleic acids from a population by a variety of selection methods. These methods may involve enrichment of the nucleic acid itself or of the one or multiple proteins encoded by that nucleic acid. Selection can be based on a growth advantage that is conferred by a mutant nucleic acid or by one or multiple proteins encoded by that nucleic acid. Alternatively, selection can be based on binding of DNA or its encoded protein to a ligand of interest using display methods such as ribosomal or phage display which are well known in the art.

The following examples are intended to exemplify preferred embodiments of the invention and are not intended to be limiting of the invention in any way, the invention being defined by the claims.

EXAMPLE

Production of a Combinatorial Mutation Library from a Subtilisin Template

The following experiment was designed to generate a library of mutants in a subtilisin template using mutagenic oligonucleotides representing 12 distinct mutations. The mutations correlating to the mutagenic oligonucleotides are shown in Table 2:

| Mutation | direction of mutagenic oligo |
| --- | --- |
| V4E | Forward |
| G20R | Forward |
| N62D | Forward |
| S87R | Forward |
| Q109R | Forward |
| S166D | Forward |
| N184D | Reverse |
| Q206R | Reverse |
| T213R | Reverse |
| L217E | Reverse |
| N261R | Reverse |
| R275H | Reverse |

All mutagenic oligonucleotides were 27 bp length. In the center they had the codon for the novel amino acid which was flanked by 12 bp on the 5' end and 12 bp one the 3' end. An example oligonucleotide sequence is N62D: correlating to the oligonucleotide ACTCAAGATGGG GATGGGCATGGCACG (SEQ ID NO:1) where the underlined codon provides the mutation. PCR was performed using as a template a gene which encodes subtilisin derived from *Bacillus lentus*. An equimolar mix of 12 mutagenic and two external non-mutagenic oligonucleotides were added as primers. The total concentration of oligonucleotides was 125 nM (approximately 9 nM for each primer). The final concentrations of the rest of the reaction components are as follows: 1×XL buffer II (PE Applied Biosystems), 0.2 mM dNTPs 1.1 mM Mg(OAc), 1 µl 1:100 diluted mini-prep plasmid DNA, 4Units rTth DNA Polymerase XL, all in a final 100 µl volume. The PCR was performed running 30 cycles of 94° C., 15 s; 30° C., 60 s; 68° C., 60 s. The resulting product was used as template for another round of PCR using only the two external non-mutagenic primers at final concentration of 1.25 µM. Finally, the product was cloned and transformed into competent Bacillus subtilis.

Eight clones were randomly chosen from the resulting library and the DNA sequence was determined.

Mutations obtained in the small sample selected are listed in Table 3.

| clone | Mutations |
| --- | --- |
| 1 | N62D/A88A/L217E/M222V |
| 2 | G20R/Q109R/S166D/N261H |
| 3 | L217E |
| 4 | G20R/S166D |
| 5 | Q109R/V139V/N184D/T213R/L217stop/N261R |
| 6 | N62D/L217E/N261R/Y263C |
| 7 | V4E/N62D |
| 8 | V4E/L41L/Q109R |

Mutations which are underlined result from the mutagenic oligonucleotides. Several of the clones contain additional mutations which probably represent non specific PCR mutations. As shown in Table 3, mutations in the selected clones were introduced in a random combinatorial distribution. Nine of the twelve mutations were observed at least once among the sequenced clones. All but one of the selected clones contain multiple mutations indicating the efficacy of the method to establish a combinatorial mutation strategy.

What is claimed is:

1. A method of producing a library of mutant nucleic acid molecules comprising:
   (a) obtaining a template nucleic acid;
   (b) preparing an oligonucleotide primer pair corresponding to the ends of said template nucleic acid;
   (c) preparing a first and a second mutagenic oligonucleotide primer, wherein said first primer corresponds to a first desired mutation within said template nucleic acid, and said second primer corresponds to a second desired mutation within said template nucleic acid;
   (d) mixing the oligonucleotide primers prepared in said steps (b) and (c); and
   (e) combining said mixture in said step (d) with the template nucleic acid under conditions to facilitate the polymerase chain reaction, wherein said mutagenic oligonucleotides are present in a concentration that is less than saturation concentration.

2. The method according to claim 1, wherein said template nucleic acid consists essentially of a single nucleic acid.

3. The method according to claim 1, wherein the mixture of said step (d) comprises at least two primers selected from the group consisting of said non-mutagenic oligonucleotide primers produced in said step (b), and said first and said second mutagenic primers produced in said step (c).

4. The method according to claim 1, wherein said template nucleic acid encodes a desired protein product.

5. The method according to claim 4, wherein said protein product is selected from the group consisting of an enzyme, hormone, vaccine, antibody, ligand or receptor.

6. The method according to claim 1, wherein said mutagenic oligonucleotide primers in said step (c) are added in a pre-defined ratio so as to bias the resulting nucleic acid library.

7. The method according to claim 6, wherein said mutagenic oligonucleotide primers in said step (c) are combined with corresponding non-mutagenic oligonucleotide primers in a pre-defined ratio so as to bias the resulting nucleic acid library.

8. The method according to claim 4, further comprising the steps of:
   (f) transforming said mutant template nucleic acid from said library into a competent host cell;
   (g) expressing protein corresponding to said mutant nucleic acid in said host cell;
   (h) screening said expressed proteins for desired characteristics.

9. The method of claim 8, wherein said transformation in said step (f) is performed using direct transformation of the products of said step (e).

10. The method according to claim 2, further comprising the steps of:
   (f) translating said mutant template nucleic acid from said library in vitro to yield an expressed protein;
   (g) screening said expressed proteins for desired characteristics.

* * * * *

SEQUENCE LISTING

```
<160> NUMBER OF SEQ ID NOS: 1

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 1
actcaagatg gggatgggca tggcacg                                             27
```